US008649862B2

(12) United States Patent
Ludwig et al.

(10) Patent No.: US 8,649,862 B2
(45) Date of Patent: Feb. 11, 2014

(54) THERAPY CIRCUIT PROTECTION FOR IMPLANTABLE MEDICAL DEVICE

(75) Inventors: Jacob M. Ludwig, Isanti, MN (US); William J. Linder, Golden Valley, MN (US); Douglas J. Brandner, New Brighton, MN (US); Nicholas J. Stessman, Minneapolis, MN (US); Douglas Michael Hannan, Minneapolis, MN (US); Scott R. Stubbs, Maple Grove, MN (US); Jeffrey E. Stahmann, Ramsey, MN (US); Arthur Foster, Centerville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/166,297

(22) Filed: Jun. 22, 2011

(65) Prior Publication Data

US 2012/0004694 A1 Jan. 5, 2012

Related U.S. Application Data

(60) Provisional application No. 61/360,608, filed on Jul. 1, 2010.

(51) Int. Cl.
*A61N 1/39* (2006.01)

(52) U.S. Cl.
USPC ............................................................. 607/7

(58) Field of Classification Search
USPC ................ 607/4–5, 7–8, 27–28, 31, 115–116
See application file for complete search history.

(56) References Cited

U.S. PATENT DOCUMENTS

| 4,142,533 A | 3/1979 | Brownlee et al. |
| 4,332,256 A | 6/1982 | Brownlee et al. |
| 4,595,009 A | 6/1986 | Leinders |
| 4,785,812 A | 11/1988 | Pihl et al. |
| 4,800,883 A | 1/1989 | Winstrom |
| 4,821,723 A | 4/1989 | Baker, Jr. et al. |

(Continued)

FOREIGN PATENT DOCUMENTS

| EP | 0170365 A2 | 2/1986 |
| EP | 0384430 A2 | 8/1990 |

(Continued)

OTHER PUBLICATIONS

Berdyshev, S, et al., "Intracardiac Impedance as a Method for Ventricular Volume Monitoring—Investigation by a Finite-Element Model and Clinical Data", 2010 J. Phys.: Conf. Ser. 224 012095 (http://iopscience.iop.org/1742-6596/224/1/012095).

(Continued)

*Primary Examiner* — Rex R Holmes
(74) *Attorney, Agent, or Firm* — Schwegman Lundberg & Woessner, P.A.

(57) ABSTRACT

A medical device can include a therapy circuit configured to provide a specified electrostimulation therapy to a tissue site, the specified electrostimulation therapy including a scheduled completion, the therapy circuit including a protection circuit configured to adjust specification of the electrostimulation therapy being provided so as to provide an adjusted electrostimulation therapy before the scheduled completion. The medical device can include a monitoring circuit comprising a comparator. The monitoring circuit can be configured to trigger the protection circuit to inhibit the therapy circuit when the therapy circuit output parameter exceeds the specified threshold as indicated by the comparator.

19 Claims, 7 Drawing Sheets

(56) References Cited

U.S. PATENT DOCUMENTS

| | | | |
|---|---|---|---|
| 5,002,052 | A | 3/1991 | Haluska |
| 5,003,975 | A | 4/1991 | Hafelfinger et al. |
| 5,224,475 | A | 7/1993 | Berg et al. |
| 5,431,684 | A | 7/1995 | Archer et al. |
| 5,453,698 | A | 9/1995 | Williams et al. |
| 5,549,646 | A | 8/1996 | Katz et al. |
| 5,571,141 | A | 11/1996 | McNeil et al. |
| 5,571,156 | A | 11/1996 | Schmukler |
| 5,591,218 | A | 1/1997 | Jacobson |
| 5,626,619 | A | 5/1997 | Jacobsen et al. |
| 5,645,572 | A | 7/1997 | Kroll et al. |
| 5,755,742 | A | 5/1998 | Schuelke et al. |
| 5,891,179 | A | 4/1999 | Er et al. |
| 5,897,577 | A | 4/1999 | Cinbis et al. |
| 6,208,898 | B1 | 3/2001 | Gliner et al. |
| 6,493,586 | B1 | 12/2002 | Stahmann et al. |
| 6,643,545 | B2* | 11/2003 | Ideker et al. ............ 607/7 |
| 6,668,193 | B2 | 12/2003 | Ware et al. |
| 6,721,600 | B2 | 4/2004 | Jorgenson et al. |
| 7,047,083 | B2 | 5/2006 | Gunderson et al. |
| 7,050,851 | B2 | 5/2006 | Plombon et al. |
| 7,211,884 | B1 | 5/2007 | Davis et al. |
| 7,242,981 | B2 | 7/2007 | Ginggen |
| 7,283,863 | B2 | 10/2007 | Gunderson et al. |
| 7,289,851 | B2 | 10/2007 | Gunderson et al. |
| 7,369,898 | B1 | 5/2008 | Kroll et al. |
| 7,454,249 | B1 | 11/2008 | Bornzin et al. |
| 7,509,167 | B2 | 3/2009 | Stessman |
| 7,515,961 | B2 | 4/2009 | Germanson et al. |
| 7,522,957 | B2 | 4/2009 | Ostroff |
| 7,561,915 | B1 | 7/2009 | Cooke et al. |
| 7,574,259 | B1 | 8/2009 | Pei et al. |
| 7,623,930 | B2 | 11/2009 | Zeijlemaker et al. |
| 2002/0072769 | A1* | 6/2002 | Silvian et al. ............ 607/2 |
| 2002/0120307 | A1 | 8/2002 | Jorgenson et al. |
| 2002/0161406 | A1 | 10/2002 | Silvian |
| 2003/0088279 | A1 | 5/2003 | Rissmann et al. |
| 2003/0088282 | A1 | 5/2003 | Ostroff |
| 2004/0024424 | A1 | 2/2004 | Propp et al. |
| 2005/0107830 | A1 | 5/2005 | Huang |
| 2005/0288714 | A1 | 12/2005 | Ostroff |
| 2006/0167496 | A1 | 7/2006 | Nelson et al. |
| 2006/0253158 | A1 | 11/2006 | Stubbs et al. |
| 2006/0293591 | A1 | 12/2006 | Wahlstrand et al. |
| 2007/0293903 | A1 | 12/2007 | Bohn et al. |
| 2008/0147132 | A1 | 6/2008 | Elahi et al. |
| 2009/0138058 | A1 | 5/2009 | Cooke et al. |
| 2009/0157132 | A1 | 6/2009 | Linder et al. |
| 2009/0157137 | A1 | 6/2009 | Gilkerson et al. |
| 2009/0157146 | A1 | 6/2009 | Linder et al. |
| 2009/0177110 | A1 | 7/2009 | Lyden et al. |
| 2009/0210021 | A1 | 8/2009 | Ostroff |
| 2010/0030286 | A1 | 2/2010 | Goetz et al. |
| 2011/0160808 | A1 | 6/2011 | Lyden et al. |
| 2011/0224747 | A1* | 9/2011 | Maile et al. ............ 607/5 |
| 2012/0158089 | A1 | 6/2012 | Bocek et al. |

FOREIGN PATENT DOCUMENTS

| | | |
|---|---|---|
| EP | 0824936 A1 | 2/1998 |
| WO | WO-98/23327 A1 | 6/1998 |
| WO | WO-2012/003124 A2 | 1/2012 |

OTHER PUBLICATIONS

Bernstein, Neil E, et al., "Right-sided implantation and subpectoral position are predisposing factors for fidelis lead fractures", Heart Rhythm, 6(5), Supplement, Abstract PO02-145, (May 2009), S192.

Calame, Susan, et al., "A Large Single Center Experience with Fidelis Lead Failure: Lower Impedance at Time of Lead Implantation Independently Associates with Lead Failure", Heart Rhythm, 6(5) Supplement, Abstract PO05-158, (May 2009), S385.

Ellenbogen, Kenneth A, et al., "Lead Integrity Alert Performance for Non-Sprint Fidelis® ICD Lead Fractures", Heart Rhythm, 6(5) Supplement, Abstract PO03-125, (May 2009), S248-S249.

Jain, Sandeep K, et al., "Intensified Remote Monitoring in Medtronic Fidelis Patients", Heart Rhythm, 6(5) Supplement, Abstract PO05-156, (May 2009), S384.

Krahn, Andrew D, et al., "Acceleration of Fidelis Failure Rate in the Canadian Heart Rhythm Society Device Advisories Committee Registry", Heart Rhythm, 6(5) Supplement, Abstract AB35-1, (May 2009), S74-S75.

Kreuz, Jens, et al., "Detailed Electrical Analysis of Lead Failures in a Small Scaled Right Ventricular Defibrillator Lead: Reality of Sprint Fidelis Medical Device Recalls in a Single Centre", Heart Rhythm, 6(5), Supplement, Abstract PO02-126, (May 2009), S185.

Lyne, Jonathan C, et al., "High failure rate of sprint fidelis defibrillator lead in young/ACHD patients: the Brompton & Harefield experience", Heart Rhythm, 6(5), Supplement, Abstract AB12-1, (May 2009), S23.

Morrison, Thomas B, et al., "Risk Factors for Fidelis and non-Fidelis Implantable Defibrillator Lead Failure", Heart Rhythm, 6(5) Supplement, Abstract AB39-4, (May 2009), S84-S85.

Nguyen, Bich Lien, "High Sensing Integrity Counter with a Sprint Fidelis™ Defibrillation Lead and a Cardiac Contractility Modulation Device: False Indication of High Voltage Lead Failure", Heart Rhythm, 6(5) Supplement, Abstract PO02-166, (May 2009), S200.

Patel, Amisha S, et al., "Modification to Lead Integrity Alert Improves Performance", Heart Rhythm, 6(5) Supplement, Abstract PO06-131, (May 2009), S438.

"International Application Serial No. PCT/US2011/041414, International Search Report mailed Dec. 29, 2011", 6 pgs.

"International Application Serial No. PCT/US2011/041414, Invitation to Pay Additional Fees mailed Nov. 9, 2011", 8 pgs.

"International Application Serial No. PCT/US2011/041414, Written Opinion mailed Dec. 29, 2011", 13 pgs.

"U.S. Appl. No. 13/297,785, Restriction Requirement mailed Feb. 21, 2013", 9 pgs.

"International Application Serial No. PCT/US2011/041414, International Preliminary Report on Patentability mailed Jan. 17, 2013", 14 pgs.

"U.S. Appl. No. 13/297,785, Non Final Office Action mailed Jun. 26, 2013", 9 pgs.

"U.S. Appl. No. 13/297,785, Response filed Apr. 1, 2013 to Restriction Requirement mailed Feb. 21, 2013", 7 pgs.

"Australian Application Serial No. 2011271590, First Examiner Report mailed Aug. 23, 2013", 6 pgs.

* cited by examiner

THERAPY CIRCUIT PROTECTION FOR IMPLANTABLE MEDICAL DEVICE

CROSS REFERENCE TO RELATED APPLICATIONS

This application claims benefit of priority under 35 U.S.C. 119(e) to Ludwig et al., U.S. Provisional Patent Application Ser. No. 61/360,608, entitled "Therapy Circuit Protection for Implantable Medical Device," filed on Jul. 1, 2010, which is presently expired, and which is hereby incorporated herein by reference in its entirety.

BACKGROUND

A heart can be considered the center of a circulatory system within a body. For example, the heart can take deoxygenated blood from elsewhere in the body and provide it to the lungs to be oxygenated. The heart can then supply the oxygenated blood from the lungs to other parts of the body. In a healthy heart, each chamber generally contracts in a coordinated fashion, such as to provide adequate circulation of oxygenated blood and nutrients to sustain the body.

The heart can be affected by a variety of physical and electrical abnormalities. Physical abnormalities can include, among other things, enlarging of the heart, sometimes associated with ischemia. Electrical abnormalities can include, among other things, various arrhythmias, such as due to infarcts, congenital defects, aging, or one or more other factors. Certain arrhythmias can be life threatening, such as including a ventricular tachyarrhythmia or ventricular fibrillation. In some patients, such life threatening arrhythmias can be detected and terminated using low-energy electrical impulses, such as provided by an implantable pulse generator. Such low-energy electrical impulses can include anti-tachyarrhythmia pacing (ATP), but such pacing is not always indicated or effective for termination of a particular arrhythmia. In cases where ATP is not indicated, or is ineffective, a defibrillation countershock can be provided, such as by an automatic implantable cardioverter defibrillator (AICD). An AICD can provide the defibrillation countershock subcutaneously, epicardially, or using one or more intravascularly-deliverable implantable leads such as located within or near the heart or vasculature.

A fault in the AICD, or in an attached lead or electrode assembly can prevent delivery of cardioversion or defibrillation countershock energy. In some situations, such a fault can present a relatively low electrical impedance to an output circuit included in the AICD. The output circuit can be stressed or permanently damaged while attempting to provide the defibrillation countershock energy into the low impedance.

United States Patent Publication No. 2004/0024424 (Propp et al.) discloses an apparatus and method of measuring a lead impedance of a high energy shock lead before delivery of a high energy therapy to treat a heart arrhythmia, including aborting a prospective delivery of the high energy therapy when a shorted lead is detected.

U.S. Pat. No. 5,224,475 (Berg et al.) discloses an implantable defibrillator provided with a plurality of defibrillation electrodes, which may be reconfigured to define a plurality of defibrillation "pathways." Berg discloses use of impedance measurements during delivery of high voltage cardioversion or defibrillation pulses to detect overall changes in the performance of the defibrillation pathway between the electrodes, for the purpose of optimization of current density when multiple defibrillation pathways are used simultaneously.

U.S. Pat. No. 5,453,698 (Williams et al.) discloses a method and system for testing an implantable defibrillator output stage and high voltage lead integrity, using a 10-20 Volt pulse discharged from a capacitor through the output stage and leads. Williams discloses measuring a residual voltage remaining on the capacitor after the discharge for comparison with a prior residual voltage measurement.

Overview

A fault in an automatic implantable cardioverter defibrillator (AICD), or in an attached lead or electrode assembly, can inhibit or prevent delivery of an electrostimulation therapy, such as a cardioversion or defibrillation countershock therapy. In some situations, such a fault can present a relatively low electrical impedance to an output circuit included in the AICD. The output circuit can be stressed or permanently damaged while attempting to provide the defibrillation countershock energy into the low impedance. In an illustrative example, a relatively low load impedance of about 10 Ohms or less can be provided to the output circuit, such as during a fault. In such a low impedance example, the output circuit can be forced to supply hundreds of amps of current instantaneously, damaging or destroying the output circuit. Such a fault can be transient or persistent, or can depend on the applied voltage. Thus, the present inventors have recognized, among other things, that a defect or fault in the AICD output path can be difficult to detect if energy levels are used that do not mimic the levels used for actual therapy. For example, insulating materials or semiconductor devices can exhibit non-linear voltage breakdown characteristics, such performing without fault if operated below the breakdown voltage. Detection of a defect or fault in such insulation or semiconductor devices can be more reliable if test voltages at or in excess of expected breakdown voltages are used, versus lower voltage measurements.

The present inventors have also recognized that monitoring an output circuit parameter during therapeutic delivery of an electrostimulation can provide useful diagnostic information since the therapy delivery can include energy levels (e.g., voltages, or currents) more likely to elicit a fault or defect in the output path, including faults in one or more of circuitry, attached leads, electrodes, interconnects, or the like. In the presence of a fault or defect detected during therapy delivery (e.g., a short circuit), the output circuitry can be disabled or otherwise inhibited (e.g., truncating or cutting off electrostimulation), such as to prevent damage or destruction of the output circuitry or other components used for therapy delivery. Since some arrhythmias can be life threatening, the present inventors have also recognized that therapy delivery might still be desired despite a fault, and thus the output circuitry can be enabled to at least attempt to deliver the complete specified electrostimulation therapy despite the fault, such as after one or more corrective or remedial action have been taken and have otherwise failed.

Example 1 includes subject matter, such as an apparatus, comprising a medical device including a therapy circuit configured to provide a specified electrostimulation therapy to a tissue site, the specified electrostimulation therapy including a scheduled completion, the therapy circuit including a protection circuit configured to adjust specification of the electrostimulation therapy being provided so as to provide an adjusted electrostimulation therapy before the scheduled completion. In Example 1, the subject matter can include a monitoring circuit comprising a comparator, the monitoring circuit configured to monitor a therapy circuit output parameter using the comparator during providing the specified electrostimulation therapy, the comparator configured to compare the therapy circuit output parameter with a specified threshold, and the monitoring circuit configured to trigger the protection circuit to adjust specification of the electrostimulation when the therapy circuit output parameter exceeds the specified threshold as indicated by the comparator.

In Example 2, the subject matter of Example 1 can optionally include a protection circuit configured to inhibit the therapy circuit from completing the specified electrostimulation therapy.

In Example 3, the subject matter of any one or more of Examples 1-2 can optionally include a monitoring circuit having a latency of about 1 microsecond or less, the latency comprising an interval beginning when the therapy circuit output parameter exceeds the specified threshold and ending with an assertion of a trigger to the protection circuit by the monitoring circuit to inhibit the therapy circuit. In Example 4, the subject matter of any one or more of Examples 1-3 can optionally include a processor circuit, and the monitoring circuit and the protection circuit can be configured to operate asynchronously with respect to the processor circuit.

In Example 5, the subject matter of any one or more of Examples 1-4 can optionally include a processor circuit, the monitoring circuit coupled to the processor circuit and configured to provide information to the processor circuit indicative of a fault when the therapy circuit output parameter exceeds the specified threshold as indicated by the comparator.

In Example 6, the subject matter of any one or more of Examples 1-5 can optionally include a processor configured to enable the therapy circuit to at least attempt to complete the specified electrostimulation therapy, despite the information indicative of the fault, when an override is asserted.

In Example 7, the subject matter of any one or more of Examples 1-6 can optionally include a counter configured to count a number of faults, and a processor configured to enable the therapy circuit to at least attempt to complete the specified electrostimulation therapy when the count of the number of faults exceeds a specified count.

In Example 8, the subject matter of any one or more of Examples 1-7 can optionally include a processor including a timer configured to measure an arrhythmia episode duration, the processor is configured to enable the therapy circuit to at least attempt to complete the electrostimulation therapy when the arrhythmia episode duration exceeds a specified duration, despite the information indicative of a fault.

In Example 9, the subject matter of any one or more of Examples 1-8 can optionally include a therapy circuit configured to provide an electrostimulation therapy using an adjusted electrostimulation therapy output parameter provided by the processor using the information indicative of a fault, the adjusted electrostimulation therapy output parameter including one or more of an adjusted current, an adjusted voltage, an adjusted power, or an adjusted energy, as compared to a specified therapy output parameter that would be provided in the absence of the fault.

In Example 10, the subject matter of any one or more of Examples 1-9 can optionally include an adjusted therapy output parameter comprising a reduced voltage as compared to a specified therapy output voltage that would be provided in the absence of the fault.

In Example 11, the subject matter of any one or more of Examples 1-10 can optionally include a therapy circuit configured to controllably provide the electrostimulation therapy to one or more of a first electrode combination at or near the tissue site, or to a second electrode combination, using an electrode selection provided by the processor circuit, and using the information indicative of a fault.

In Example 12, the subject matter of any one or more of Examples 1-11 can optionally include a therapy circuit comprising a conductor, the therapy circuit output parameter including an output current through the conductor, and a comparator configured to compare a voltage developed across a specified portion of the conductor with the specified threshold.

In Example 13, the subject matter of any one or more of Examples 1-12 can optionally include a medical device comprising an implantable medical device, the system further comprising an implantable lead electrically and mechanically coupled to the implantable medical device, the implantable lead including an electrode implantable at or near the tissue site.

In Example 14, the subject matter of any one or more of Examples 1-13 can optionally include a therapy circuit comprising an insulated gate bipolar transistor (IGBT), the therapy circuit is configured to provide the electrostimulation therapy at least in part using the IGBT, and a protection circuit configured to control a gate of the IGBT to inhibit conduction of the electrostimulation therapy in response to a trigger provided by the monitoring circuit.

In Example 15, the subject matter of any one or more of Examples 1-14 can optionally include a therapy circuit comprising an insulated gate bipolar transistor (IGBT) coupled to a gate-turn-off (GTO) thyristor, the therapy circuit configured to provide the electrostimulation therapy at least in part using the GTO thyristor, and at least in part using the IGBT to control the conduction state of the GTO thyristor, and a protection circuit configured to control a gate of the IGBT to inhibit conduction of the electrostimulation therapy by the GTO thyristor in response to a trigger provided by the monitoring circuit.

Example 16 can include, or can optionally be combined with the subject matter of one or any combination of Examples 1-15 to include, subject matter (such as a method, a means for performing acts, or a machine- or device-readable medium including instructions that, when performed by the machine or device, cause the machine or device to perform acts comprising providing a specified electrostimulation therapy to a tissue site using a therapy circuit, the specified electrostimulation therapy including a scheduled completion, monitoring a therapy circuit output parameter using a monitoring circuit during the providing the specified electrostimulation therapy, including comparing a therapy circuit output parameter to a specified threshold, and adjusting the specification of the electrostimulation therapy being provided using a protection circuit when the therapy circuit output parameter exceeds the specified threshold so as to provide an adjusted electrostimulation therapy before the scheduled completion.

In Example 17, the subject matter of Example 16 can optionally include operating the monitoring circuit and the protection circuit asynchronously with respect to a processor circuit.

In Example 18, the subject matter of any one or more of Examples 16-17 can optionally include providing information indicative of a fault to the processor circuit in response to the therapy output parameter exceeding the specified threshold, and enabling the therapy circuit to at least attempt to complete the specified electrostimulation therapy despite the information indicative of the fault.

In Example 19, the subject matter of any one or more of Examples 16-18 can optionally include counting a number of faults, and enabling the therapy circuit to at least attempt to complete the specified electrostimulation therapy despite the information indicative of a fault when a count of the number of faults exceeds a specified count.

In Example 20, the subject matter of any one or more of Examples 16-19 can optionally include measuring an arrhythmia episode duration, enabling the therapy circuit to at least attempt to complete the specified electrostimulation therapy despite the information indicative of a fault when the arrhythmia episode duration exceeds a specified duration.

In Example 21, the subject matter of any one or more of Examples 16-20 can optionally include providing an electrostimulation therapy using an adjusted electrostimulation therapy output parameter provided by the processor in response to the information indicative of a fault, the adjusted electrostimulation therapy output parameter including one or more of an adjusted current, an adjusted voltage, an adjusted power, or an adjusted energy, as compared to a specified therapy output parameter that would be provided in the absence of the fault.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
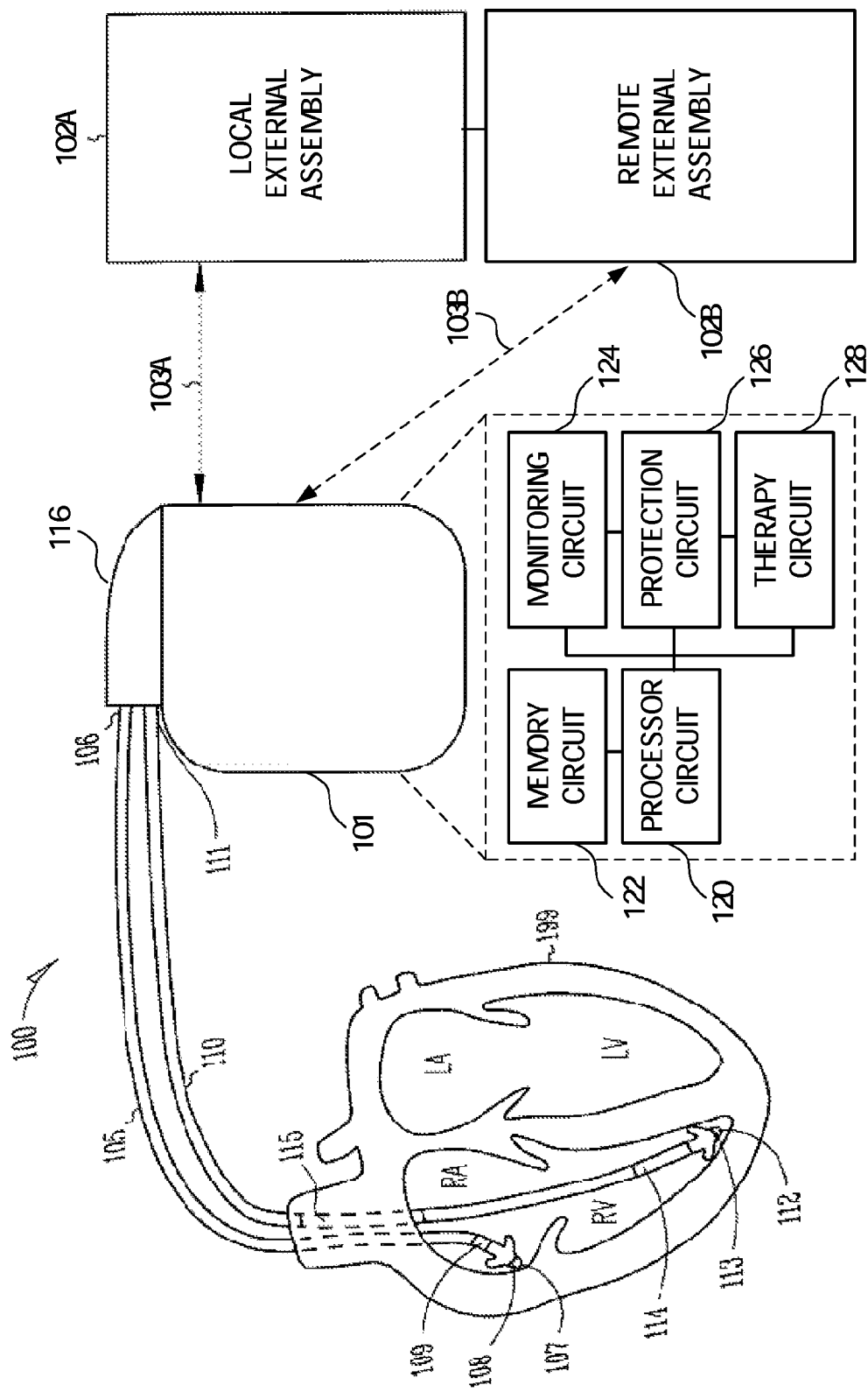
FIG. 1 illustrates generally an example of a portion of a cardiac function management system.

FIG. 1 illustrates generally an example of at least a portion of a cardiac function management system 100 that can include an implantable medical device (IMD) 101. The IMD can comprise an automatic implantable cardioverter defibrillator (AICD), a cardiac resynchronization therapy device including defibrillating or cardioverting capabilities, or other monitoring or therapeutic capabilities. While the example of FIG. 1 shows an IMD, such as a cardiac function management device, the discussion can also be relevant to other types of IMDs, such as attached to elongated leads or conductors, such as in other locations.

In an example, the IMD 101 can be electrically coupled to a heart 199 such as using one or more leads, such as a first lead 105 or a second lead 110. One or more external assemblies can communicate with the IMD 101, such as a local external assembly 102A (e.g., a bedside monitor, a patient-worn monitor, a physician programmer, or the like), or a remote external assembly 102B (e.g., a remote server or web-based user interface such as included on a personal computer). One or more external assemblies can transfer information, such as physiologic information, configuration or fault information, or other data between the IMD 101 and the respective local or remote external modules 102A and 102B, such as using a first or second respective communication links 103A or 103B. In an example, the respective communication links 103A or 103B can be wireless (e.g., acoustic, electromagnetic, magnetic, optical, etc.) or wired (e.g., using body conduction, or one or more other wired networking links).

In an example, the first lead 105 can be used as a pacing lead, such as including a proximal end 106 connected to IMD 101 and a distal end 107, such as placed in the right atrium (RA) of heart 199. An atrial tip electrode 108 can be located at the distal end 107. In the example of FIG. 1, an atrial ring electrode 109 can locate near distal end 107 as well. In an example, the respective tip and ring electrodes 108 and 109 can be electrically connected to IMD 101, such as via separate conductors in lead 105, such as to provide bipolar sensing of the atrial cardiac activity or bipolar delivery of atrial pacing pulses. In an example, the one or more separate conductors in lead 105 can be attached or secured to one or more terminal blocks included in a header block 116, such as to provide electrical contact between the lead 105 conductors, and circuitry within the IMD 101. In an example, the IMD 101 can be attached to one or more other leads or conductors, such as when the IMD 101 includes a cardiac resynchronization therapy (CRT) circuit. In a CRT example, the IMD 101 can be attached to one or more leads configured for intravascular delivery to a great vein of the heart, such as through the ostium of the coronary sinus, such as to provide pacing or sensing at various locations near the left ventricle of the heart. In an example, the atrial tip electrode 108 can be used along with the housing of the IMD 101, such as to provide unipolar sensing of atrial cardiac activity, or unipolar delivery of atrial pacing pulses. In an example, the IMD 101 can include one or more circuits or programmable parameters allowing the IMD to be controllably configured for unipolar or bipolar pacing or sensing.

In an example, the second lead 110 can be a endocardial defibrillation lead, such as including a proximal end 111 connected to IMD 101 and a distal end 112, such as placed in the right ventricle (RV) of heart 199, or elsewhere (e.g., in the atrium, or included as a portion of the atrial lead 105. For example, the second lead 110 can include a right ventricular (RV) distal tip electrode, such as located at or near the apical region of the RV chamber, near the distal end 112 of the RV lead. In FIG. 1, an RV coil electrode 114 can be located near distal end 112 but can be electrically separated from the RV distal tip electrode 113. In an example, a superior vena cava (SVC) coil electrode 115 can be located at a distance from distal end 112.

In an example, the respective electrodes 113-115 can be electrically connected to IMD 101, such as via separate conductors in lead 110, such as attached or secured to one or more terminal blocks included in the header block 116 of the IMD. For example, the respective RV tip electrode 113 and RV coil electrode 114 can be used for bipolar sensing of the ventricular cardiac electrical activity or for delivery of ventricular electrostimulation pulses. In an example, one or more of the RV coil electrode 114, the SVC coil electrode 115, or the device housing can be used for sensing of cardiac electrical activity or for delivery of ventricular tachyarrhythmia therapy (e.g., one or more of anti-tachyarrhythmia pacing, cardioversion, shock, or the like).

One or more of the first or second communication links 103A or 103B can provides wireless information transmission between the IMD 101 and various implanted or external devices. For example, one or more of real-time physiological data acquired by IMD 101, physiological data acquired by and stored in IMD 101, therapy history data stored in IMD 101, information indicating an operational status of IMD 101 (e.g., battery status and lead impedance), or other information can be transferred. In an example, information transferred to the IMD 101 can include instructions programming IMD 101 to acquire physiological data, programming IMD 101 to perform at least one self-diagnostic test (such as for a device operational status, or an isolation test), programming IMD 101 to run a signal analysis algorithm (e.g., an algorithm implementing a tachyarrhythmia classification method) or programming IMD 101 to deliver one or more pacing or tachyarrhythmia therapies, among other instructions.

In an example, the IMD 101 can include a hermetically sealed housing, such as containing electronic circuitry. In an example, the circuitry can include one or more portions, such as a circuit to sense or condition physiological signals, or a circuit to provide one or more electrostimulation therapies (e.g., to one or more cardiac or neural targets). In an example, the hermetically sealed housing itself can also function as an electrode for use in sensing physiologic information (e.g., electrically or mechanically), or for use as an electrode for electrostimulation delivery.

FIG. 1 shows an IMD 101 that can include a memory circuit 122, a processor circuit 120, a therapy circuit 128, a protection circuit 126, and a monitoring circuit 124, such as similarly discussed below in the examples of FIGS. 2-3. The therapy circuit 128 can include a defibrillation or cardioversion therapy delivery circuit, such as configured to provide a specified electrostimulation therapy. The monitoring circuit 124 can be configured to monitor a therapy circuit output parameter, such as before or during delivery of a specified electrostimulation therapy (e.g., a defibrillation countershock, or the like). The output parameter can include one or more of a voltage or current, and the monitoring circuit can be configured to trigger the protection circuit 126 when the voltage or current is outside a specified range, such as before or during delivery of the specified electrostimulation. In an example, the protection circuit 126 can inhibit or terminate (e.g., truncate or cut off) delivery of the electrostimulation therapy by the therapy circuit 128, such as in response to assertion of a trigger by the monitoring circuit 124. In an example, one or more faults detectable by the monitoring circuit can include a short or open circuit condition, such as within the therapy circuit 128, or elsewhere in the therapy output path (e.g., within or between the first or second leads 105 and 110, or involving interconnect defects in the header 116, or within the housing of the IMD 101, among others).

In an example, the internal circuitry of IMD 101, including its various elements discussed in this document, can include a combination of hardware and software. For example, one or more portions, elements, or circuits included in IMD 101 can be implemented, such as using an application-specific circuit constructed to perform one or more particular functions or a general-purpose circuit programmed to perform such function(s). Such a general-purpose circuit (e.g., the processor circuit 120) can include, but is not limited to, a microprocessor or a portion thereof, a microcontroller or portions thereof, and a programmable logic circuit or a portion thereof, such as configured to execute or otherwise perform instructions stored within or on a medium readable by the IMD 101 (e.g., a device-readable medium), such as the memory circuit 122.

Figure 2:
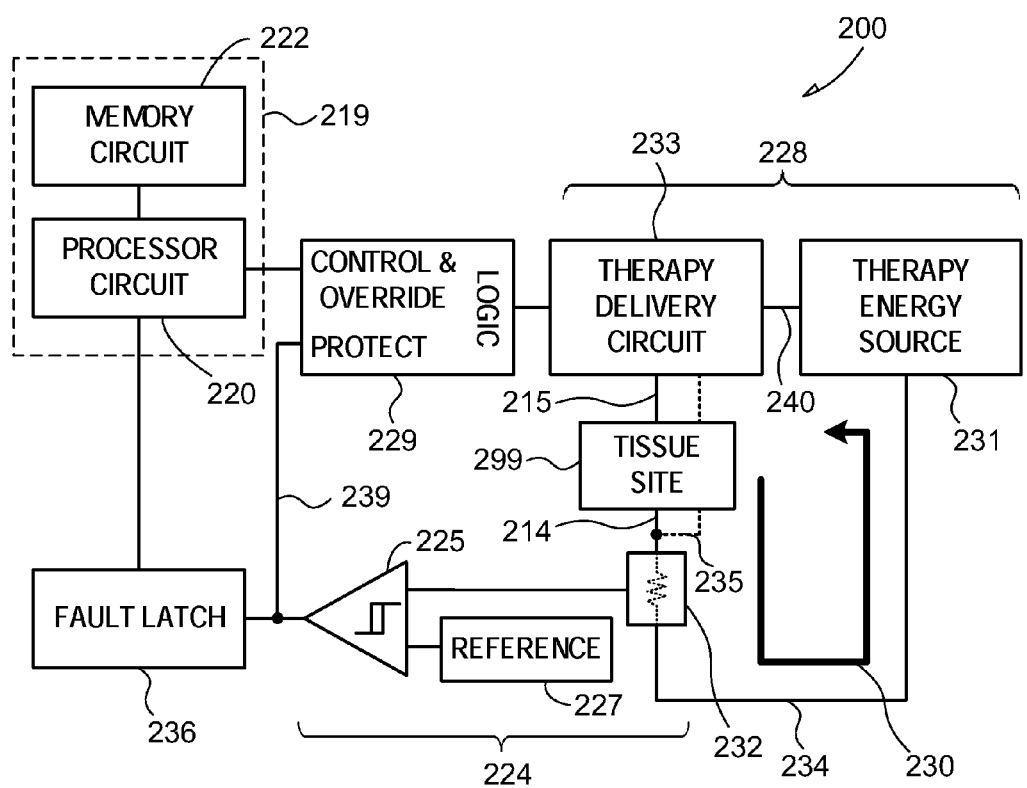
FIG. 2 illustrates generally an example of a portion of an automatic implantable cardioverter defibrillator (AICD), such as including a portion of the system shown in the example of FIG. 1.

FIG. 2 illustrates generally an example of at least a portion of an automatic implantable cardioverter defibrillator (AICD) 200, such as included as portion of the system shown in the example of FIG. 1. In FIG. 2, the AICD 200 can include a memory circuit 222 coupled to a processor circuit 220, a control circuit 229 such as including a triggerable protection circuit, a therapy delivery circuit 233, a therapy energy source 231, a comparator 225, a reference 227, a sensing element 232, and a fault latch 236. In an example, the therapy delivery circuit 228 and therapy energy source 231 be included in a therapy circuit 233, such as electrically coupled together and configured to provide a cardioversion or defibrillation countershock therapy, similar to the therapy circuit 128 of FIG. 1. One or more therapy output parameters can be controlled, such as using the processor circuit 220, via the control circuit 229. Such adjustable therapy output parameters can include, for example, a defibrillation pulse duration, an output wave shape or number of pulses, a peak voltage, a peak current, or total energy to be delivered, such as to a tissue site 299 (e.g., a heart), via a first conductor 215, or a second conductor 214. For example, one or more of the first or second conductors 214 or 215 can be respectively coupled to one or more respective electrodes such as included on or within one or more endocardial leads located within the heart as shown in FIG. 1, or at one or more other locations. For example, the therapy delivery circuit 233 can be configured to use a first electrode combination including the first and second conductors 214 and 215, or a second electrode combination such as including the path 235, such as in response to a user command, or in response to a detected fault or defect in the path 230 including the first combination.

One or more other defibrillation waveforms can be provided using the circuitry of FIG. 2, such as one or more monophasic, biphasic, triphasic, or multi-phasic waveforms such as discussed in U.S. Pat. No. 4,800,883, entitled "Apparatus for generating multi-phasic defibrillation pulse waveform," filed Apr. 2, 1986, or U.S. Pat. No. 4,821,723, entitled "Biphasic waveforms for defibrillation," filed Apr. 18, 1989, both of which are assigned to Intermedics, Inc., and both of which are herein incorporated by reference in their respective entireties.

In an example, a monitoring circuit 224 can include one or more of the comparator 225, the reference 227, or the sensing element 232. For example, the sensing element 232 can be a discrete or parasitic resistance in line with a therapy output path 230. The therapy output path 230 can include one or more of the therapy circuit 228, the first or second conductors 214 or 215, the tissue site 299, one or more interconnects such as a connection 240 between the therapy delivery circuit and the therapy energy source 231, or a return path 234. In an example, the return path 234 or other portions of the output path 230 can be provided at least in part by a wire or trace on a printed wiring board (e.g., a flexible or rigid circuit assembly). For example, the output path 230 can include a substantially closed current path, including the sensing element 232. The sensing element 232 can be a portion of a wire or trace, such as configured to provide a signal (e.g., a voltage) proportional to the current flowing during the delivery of electrostimulation therapy using the therapy delivery circuit 233. In an example, the sensing element 232 can be a trimmable resistor, such as including a laser-trimmable thin-film resistor, a polysilicon resistor included as a portion of an integrated circuit or multi-chip module, or including one or more other resistors.

In an example, the reference 227 can be programmed to provide a voltage or other reference signal proportional to a specified current threshold. The comparator 225 can compare a signal representative of an instantaneous output current provided by the sensing element 232 (e.g., a voltage developed across the element 232) with the specified threshold provided by the reference 227. In an example, the comparator 225 can assert a trigger 239 to a protection input of the control circuit 229, such as when the output current exceeds the specified threshold, or when another output circuit parameter is otherwise outside a specified range. The control circuit 229 can inhibit the therapy delivery circuit 233, such as when the current exceeds the specified threshold, and such as in response to a signal provided by the monitoring circuit 224. In an example where a wire or trace is used as the sensing element 232, the reference 227 can be programmable to compensate for unit-to-unit variation, or variation over time in a single unit, such as including an 8-bit digital-to-analog converter, or using one or more other circuits. For example, during manufacturing, or at other times, a therapy output parameter including a known voltage or current can be provided, and the reference 227 can be calibrated to achieve a desired threshold for the monitoring circuit 224, or a resistance of the sensing element 232 can be measured directly. In an example, a voltage provided by the therapy delivery circuit 233 can be sensed directly by the comparator, or one or more other therapy circuit output parameters can be monitored, such as to assert the trigger 239 or to provide another signal to inhibit the therapy delivery circuit 233 before or during delivery of the specified electrostimulation therapy.

The therapy delivery circuit 233, the energy source 231, or other portions along the path 230 can be damaged or destroyed if a fault or defect occurs along or the therapy output path 230. The comparator 225 and control circuit 229 can include relatively high-speed responses, such as operating asynchronously with respect to one or more of the processor circuit 220, or the memory circuit 222, or otherwise operating independently of firmware or software control. Such asynchronous operation can reduce a likelihood of damage to the therapy circuit or other portions of the system, even in the presence of an ongoing fault, as compared to inhibiting therapy or terminating therapy delivery early using synchronous operation of the processor circuit 220. In an illustrative example, the monitoring circuit 224 can include a latency of about 1 microsecond or less, the latency comprising an interval beginning when the therapy circuit 228 output parameter exceeds the specified threshold as determined by the reference 227, and the interval ending with an assertion of the trigger 239 to the protection circuit included in the control circuit 229. In an example, one or more of the monitoring circuit 224, the control circuit 229, or the therapy circuit 228 can be included in an analog or mixed-signal application specific integrated circuit (ASIC), such as fabricated for low power consumption operation using a CMOS process. For example, the processor circuit 220 and the memory circuit 222 can be included in separate or commonly-shared digital or mixed-signal integrated circuits, such as separate from one or more of the monitoring circuit 224, the control circuit 229, or the therapy circuit 228.

In an example, information indicative of a fault can be provided by the monitoring circuit 224 to the processor circuit 220, even if the monitoring circuit 224 detects the fault asynchronously to the processor circuit 220. For example, a fault can be latched using a fault latch 236, such as for later polling or retrieval by the processor circuit 220. In an example, the processor circuit can adjust one or more of therapy circuit 228 output parameters, such as in response to the information indicative of the fault. For example, the processor circuit 220 can be configured to override the protection circuit included in the control circuit 229, such as to enable delivery of therapy (e.g., at least an attempt to deliver therapy) despite the presence of a fault or defect in the output path 230.

In an example, the processor circuit 220 can include one or more timers or counters, such as a counter configured to count a number of faults, such as including one or more faults as indicated by the comparator 225 (e.g., via the fault latch 236 or using other circuitry). In an example, the processor circuit 220 can be configured to override the protection circuit included in the control circuit 229 to at least attempt to complete delivery of electrostimulation therapy despite information indicative of one or more faults, such as when the count of the number of faults exceeds a specified count. Similarly, in an example, the processor circuit 220 can be configured to measure a duration of an arrhythmia episode, such as an ongoing arrhythmia episode (e.g., a ventricular tachyarrhythmia or other arrhythmia). The processor circuit 220 can be configured to override the protection circuit included in the control circuit 229 to at least attempt to complete delivery of the electrostimulation therapy despite information indicative of the one or more faults, such as when the arrhythmia episode duration exceeds a specified duration.

Figure 3:
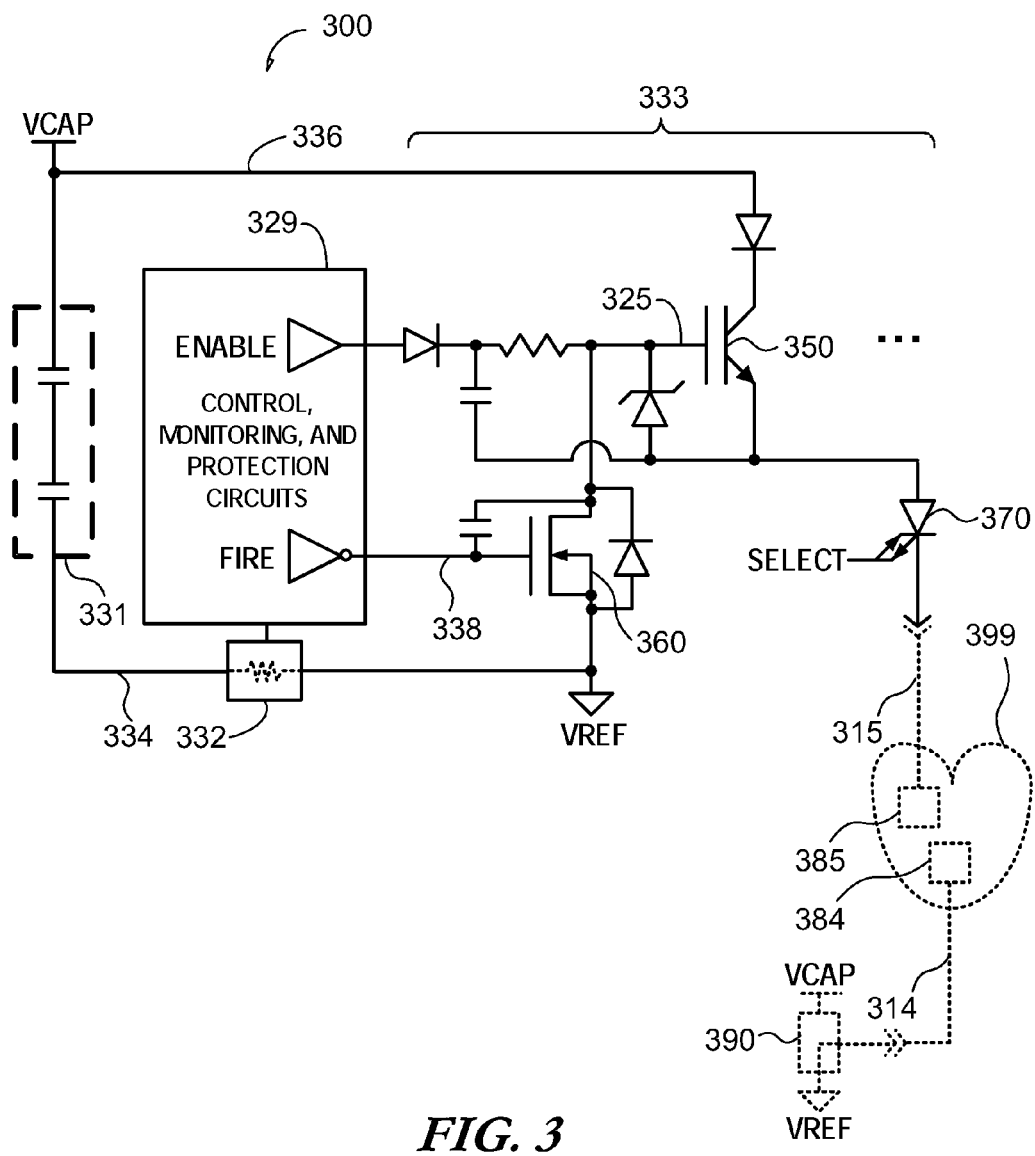
FIG. 3 illustrates generally an example of a portion of an output circuit, such as included in an automatic implantable cardioverter defibrillator (AICD) as shown in the examples of FIGS. 1-2.

FIG. 3 illustrates generally an example 300 of a portion of a therapy circuit, such as including a portion of one or more of the therapy circuits 128, 228 of an automatic implantable cardioverter defibrillator (AICD) as shown in the examples of FIGS. 1-2. In an example, the portion of the therapy circuit shown in FIG. 3 can include circuitry or methods of operation similar the examples of one or more defibrillation shock output circuits as described in U.S. patent application Ser. No. 12/332,497, entitled "Defibrillation Shock Output Circuit", filed Dec. 11, 2008, and assigned to Cardiac Pacemakers, Inc., which is herein incorporated by reference in its entirety, and specifically incorporating herein its discussion of providing a specified shock output "vector" using an output "bridge" configuration or one or more other semiconductor switching circuit configurations.

In FIG. 3, the therapy circuit can include a therapy energy source 331, such as coupled to a "high-side" switch included as a portion of an output bridge circuit, such as including an isolated gate bipolar transistor (IGBT) 350. In the example of FIG. 3, the therapy circuit can include a first portion 333 of a delivery circuit, such as including a trigger field-effect transistor (FET) 360, configured to control a conduction state of the IGBT 350. The first portion 333 can also include one or more other switches, such as a gate-turn-off (GTO) thyristor 370 (e.g., a remote gate thyristor), or one or more other controllable semiconductor devices.

In the example of FIG. 3, a first lead 315 can be coupled to a first electrode 385, such as located within or near a heart 399. For example, the first portion 333 of the delivery circuit can be used to selectively attach the first lead 315 to a first supply node VCAP via the IGBT 350 and GTO 370, or via one or more other switching devices. In an example, a second lead 314 can be coupled to a second electrode 384, such as coupled to a second supply node VREF, such as coupled to a return path 334 leading back to the energy source 331, via a second portion 390 of a therapy delivery circuit, forming a closed therapy output path.

In an example, a particular GTO, such as the GTO 370, can be "selected" or turned on, such as according to a desired lead or electrode configuration provided by a processor circuit (e.g., the processor circuit 120, or 220 of FIGS. 1-2). When the GTO 370 is selected, the first lead and the first electrode 385 can be connected to VCAP when the IGBT 350 is also turned on. In FIG. 3, one or more of a control, a monitoring, or a protection circuit 329 can provide outputs to control the conduction state of the IGBT 350, such as using the trigger FET 360. A gate input 325 to the IGBT can be controlled via a combination of an "ENABLE" output from the circuit 329, and an output to "FIRE" (e.g., to turn on) the IGBT 350 using a gate input 338 of the trigger FET 360. For example, one or more circuits or portions of the examples of FIGS. 1-2 can be used to enable or disable the IGBT 350 using the ENABLE output. In FIG. 3, when the ENABLE output is low (e.g., at around 0V or otherwise de-asserted), the FIRE output cannot turn on the IGBT 350.

In order to deliver a first phase (or a monophasic portion) of a defibrillation countershock or cardioversion pulse, the energy source 331 can first be charged, such as to a desired voltage corresponding to a specified energy level (e.g., using one or more capacitors in a series or parallel configuration, such as charged by a switched-mode inductive supply using energy provided by an implantable battery). In such a defibrillation delivery example, the GTO 370 can then be selected (e.g., turned on), and the second portion 390 of the therapy circuit can be configured to tie the second lead 314 to the second supply node VREF. Then, the IGBT 350 can be turned on for a specified duration corresponding to the desired pulse width of the defibrillation or cardioversion pulse phase. In a biphasic defibrillation example, the defibrillation or cardioversion pulse can include a second phase, such as using an opposite polarity as used during the first phase. In such a biphasic example, the IGBT 350 can be turned off, and another semiconductor switch can be used to connect the first lead 315 and the first electrode 385 to VREF. Similarly, in the biphasic defibrillation example, the second portion 390 can include circuitry similar to the first portion 333, such as to selectively connect the second lead 314 and second electrode 384 to VCAP. In an example, the second portion 390 can include a second GTO device to "select" the second lead 314, and the IGBT 350 can still be used to gate the VCAP connection to the second lead 314, since the GTO 370 can remain turned off (e.g., de-selected).

In an example, the return path between VREF and the energy source 331 can include a sensing element 332, such as coupled to one or more of the control, monitoring, or protection circuits, as discussed in FIGS. 1-2. The sensing element can configured to monitor an output parameter of the therapy circuit, such as an instantaneous current. For example, a signal proportional to the current through the sensing element 332 can be provided to the circuit 329 for comparison with a specified threshold, as in the examples of FIG. 2, and the ENABLE output can be de-asserted such as in response to a sensed current in excess of the specified threshold. For example, if a short circuit were present or developed along the therapy output path during delivery of a defibrillation or cardioversion pulse, the ENABLE output could be de-asserted, cutting off the IGBT 350 and terminating the therapy during delivery. In an example, the circuitry of FIG. 3 can operate asynchronously to a processor circuit, but the processor circuit can be configured to override the de-assertion of the ENABLE line, despite the presence or information indicative of a fault. For example, the processor could control a gate or other circuit configured to prevent the ENABLE line from being de-asserted despite the information indicative of a fault as provided by the sensing element 332, as discussed in FIGS. 1-2.

Figure 4:
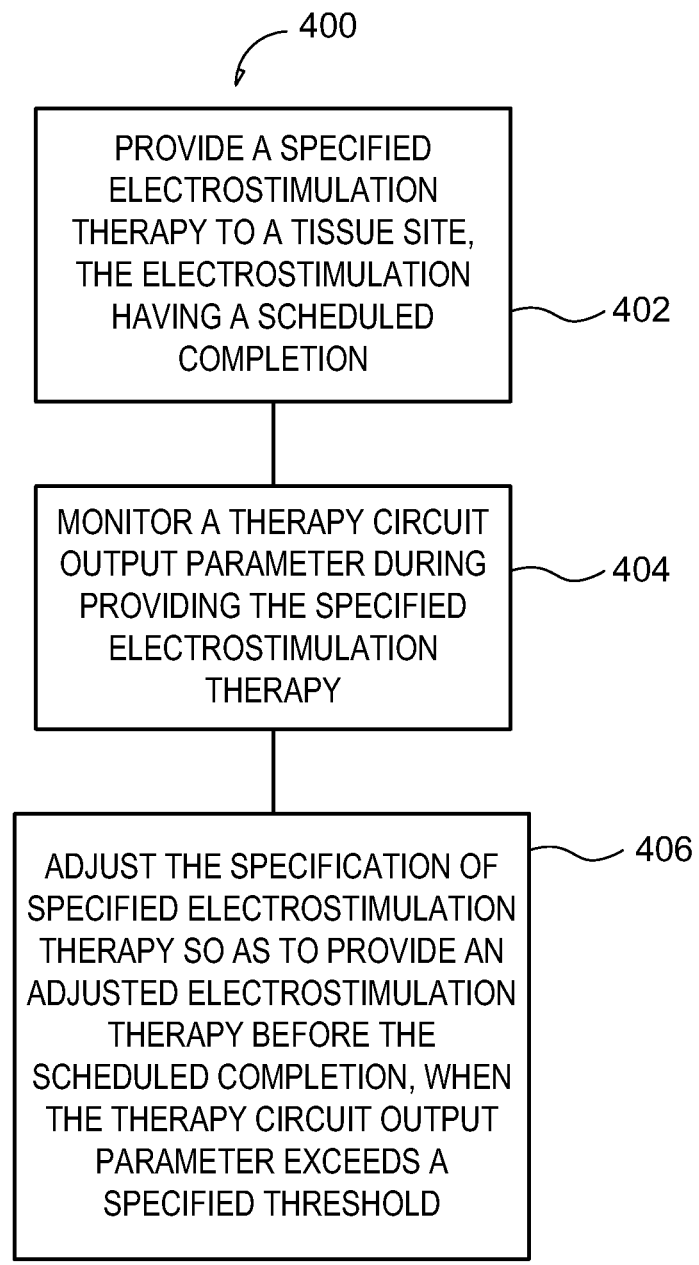
FIG. 4 illustrates generally an example that can include providing a specified electrostimulation therapy to a tissue site.

FIG. 4 illustrates generally an example 400 that can include providing a specified electrostimulation therapy to a tissue site, the electrostimulation having a scheduled completion (e.g., a completion in the absence of a fault). At 402, a therapy circuit such as including one or more of the circuits discussed above with respect to FIGS. 1-3 can be used to provide the specified electrostimulation to the tissue site. The specified electrostimulation can include a cardioversion or defibrillation pulse, such as having a specified duration, a specified number of phases, a specified voltage, a specified current, or a specified total energy, among other parameters. At 404, the therapy circuit can be monitored such as during the providing the specified electrostimulation, such as using one or more of the circuits discussed above with respect to FIGS. 1-3. For example, a therapy circuit output parameter can be monitored during providing the electrostimulation, such as using the monitoring circuit of FIG. 2 (e.g., using information from a sensing element as described in FIGS. 2-3). At 406, the electrostimulation therapy can be adjusted or inhibited, such as before completion of the specified electrostimulation therapy, and in response to the therapy circuit output parameter exceeding a specified threshold, or falling outside of a specified range. For example, the logic, control, or protection circuitry of FIGS. 1-3 can be used to inhibit the delivery of electrostimulation during or after information indicative of a fault is detected. In an example, the specification of the specified electrostimulation therapy can be adjusted during delivery (e.g., before the scheduled completion), so as to provide an adjusted electrostimulation therapy, such as when the therapy circuit output parameter exceeds the specified threshold.

Figure 5:
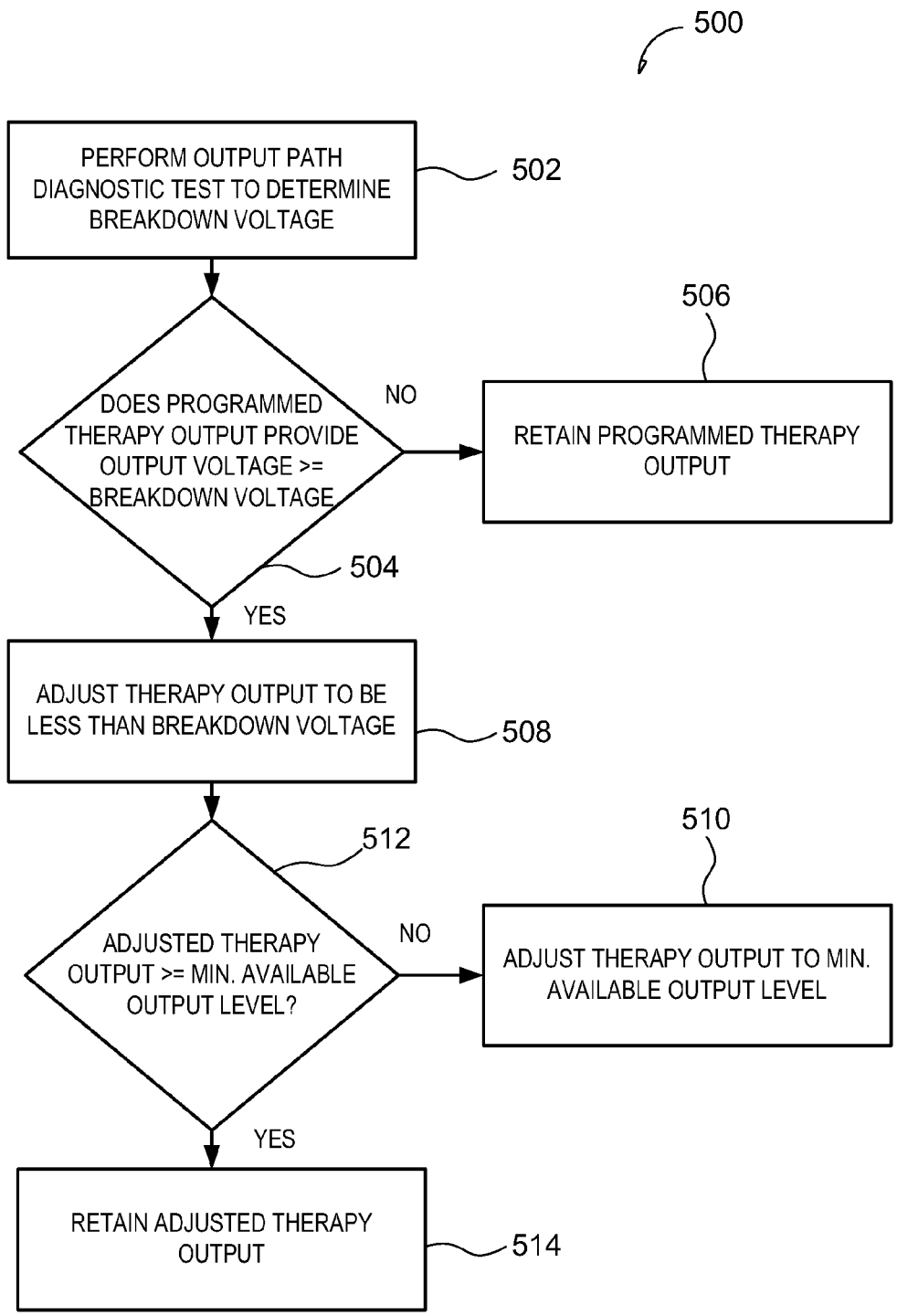
FIG. 5 illustrates generally an example that can include performing an output path diagnostic test to determine a breakdown voltage.

FIG. 5 illustrates generally an example 500 that can include performing an output path diagnostic test to determine a breakdown voltage. At 502, an output path diagnostic can be used such as to determine an output path breakdown voltage. In an example, such a diagnostic test can use a therapy circuit such as discussed above with respect to the examples of FIGS. 1-3. For example, the breakdown voltage information can be provided by monitoring output voltage during therapeutic or diagnostic delivery of one or more defibrillating or cardioverting pulses, either automatically or upon command, such as provided by a caregiver.

In an example, the output path diagnostic test can include providing the energy in a cardiosynchronous manner, such as to avoid inducing an arrhythmia. At 504, a programmed therapy output voltage can be compared with the breakdown voltage provided by the diagnostic test. At 506, if the programmed therapy output voltage is less than the breakdown voltage, the programmed therapy output voltage can be retained, such as for use in one or more subsequent therapeutic cardioversion or defibrillation pulse deliveries, such as according to the examples of one or more of FIGS. 1-4.

At 508, if the programmed therapy output voltage equals or exceeds the breakdown voltage, the output voltage can be adjusted to be less than the breakdown voltage, such as below the breakdown voltage by specified a specified offset, ratio, or other relative or absolute relationship to the breakdown voltage. At 512, the adjusted therapy output voltage can be compared with a minimum available output level (e.g., a minimum level determined to be therapeutically effective, or a minimum level determined by the capability of the therapy circuit hardware, among others). At 510, if the adjusted therapy output voltage at 508 is below the minimum available output level, the therapy output voltage can again be adjusted to be at or above the minimum available therapy output level. At 514, if the adjusted therapy output level at 508 is above or equal to the minimum available output level, the adjusted therapy output voltage can be retained, such as for use in subsequent therapy delivery.

Figure 6:
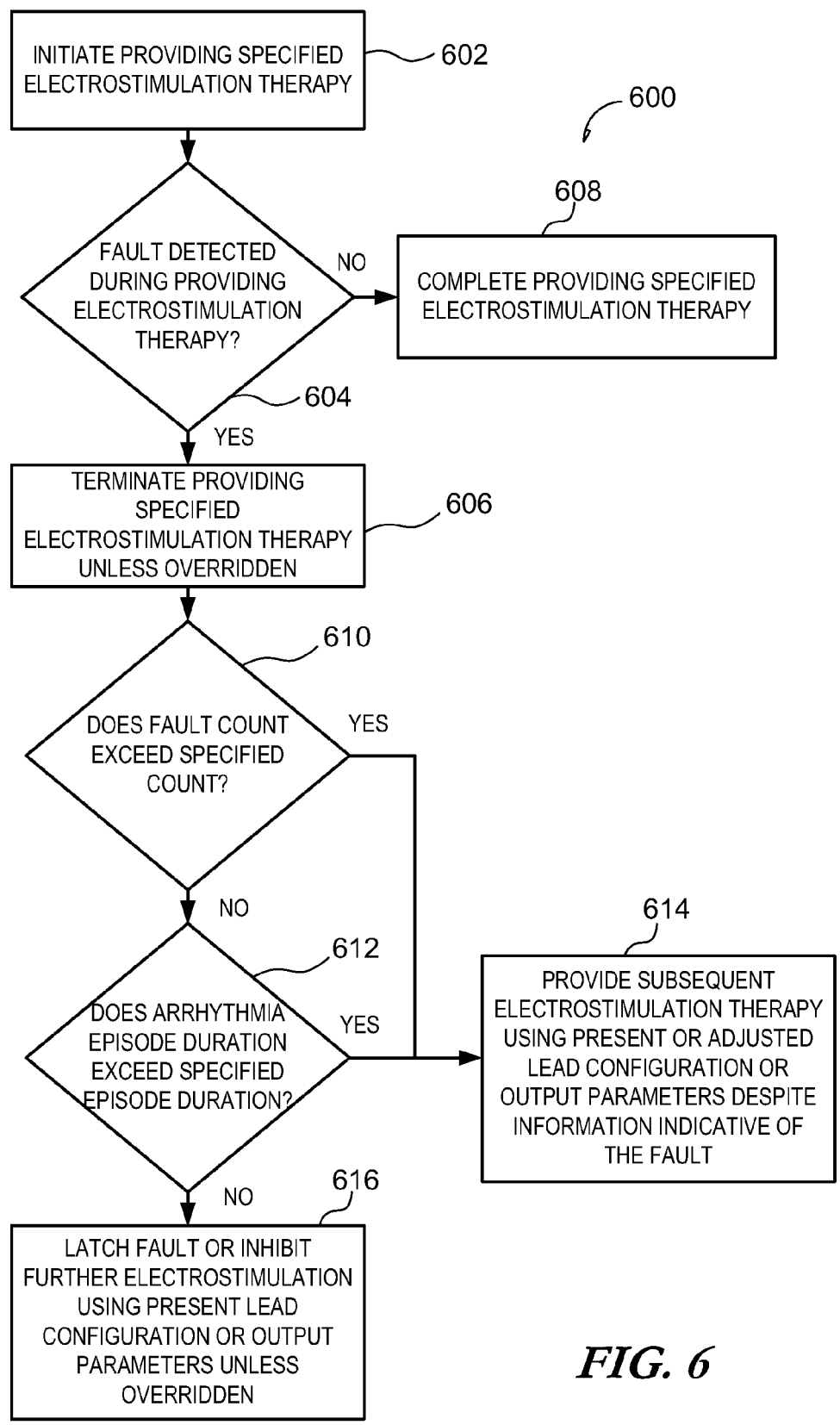
FIG. 6 illustrates generally an example that can include providing a specified electrostimulation therapy, and terminating the electrostimulation therapy if a fault is detected during providing the electrostimulation.

FIG. 6 illustrates generally an example 600 that can include providing a specified electrostimulation therapy, and terminating the electrostimulation therapy if a fault is detected during providing the electrostimulation. At 602, an electrostimulation therapy can be initiated, such as including providing a cardioversion or defibrillating pulse using a therapy circuit as shown in the examples of FIGS. 1-3. At 604, the therapy circuit can be monitored, such as using a monitoring circuit is discussed above in the examples of FIGS. 1-3. For example, one or more therapy circuit output parameters can be compared to one or more specified thresholds or ranges, such as an output current. In an example, if the output current exceeds a specified threshold, such as indicating a breakdown or short circuit condition, the monitoring circuit can provide information indicative of a fault. At 608, if no fault is detected during the providing the electrostimulation, the delivery can be completed without interruption.

At 606, if a fault is detected during providing the electrostimulation, the delivery of electrostimulation can be terminated (e.g., truncated or otherwise cut off), such as before a specified electrostimulation energy has been completely delivered during a particular arrhythmia, as discussed in the examples of FIGS. 1-3. However, in an example, termination of the electrostimulation therapy can be overridden, such as where other remedial or corrective actions have already been exhausted. For example, a number of faults can be counted. At 610, a count of the number of faults can be compared with a specified count.

Similarly, an arrhythmia episode duration can be monitored, such as using a timer or counter. At 612, the arrhythmia episode duration (e.g., for an ongoing or terminated arrhythmia) can be compared to a specified episode duration. At 614, if the number of faults exceeds the specified count, or if the arrhythmia duration exceeds the specified arrhythmia episode duration, subsequent electrostimulation therapy can at least be attempted using either the present or adjusted output parameters or lead configuration, despite the information indicative of the fault. Similarly, at 616, if the number of faults is less than or equal to the specified count, and the arrhythmia episode duration is less than or equal to the specified episode duration, then the fault can be latched, for example, and further electrostimulation using the present lead configuration or output parameters can be inhibited.

At 616, one or more remedial or corrective actions can be taken, such as under the control of a processor circuit as discussed above in the examples of FIGS. 1-3. Such corrective or remedial action can include using an adjusted electrostimulation therapy output parameter for subsequent therapy delivery, including using one or more of an adjusted current, an adjusted voltage, an adjusted power, or an adjusted energy, as compared to a specified therapy output parameter that would be provided in the absence of the fault. In an example, such corrective or remedial action can include using a reduced therapy output voltage as compared to a specified therapy output voltage that would be provided in the absence of the fault, such as discussed in the example of FIG. 5.

In an example, such corrective or remedial action can include using a different electrode combination, such as to avoid a particular electrode or lead that exhibits or has exhibited a fault. In an example, if all electrodes or lead combinations exhibit a fault, the electrostimulation therapy can still be delivered (or at least delivery can be attempted) despite the fault, such as in response to control from a processor circuit as discussed in the examples of FIGS. 1-3.

Figure 7:
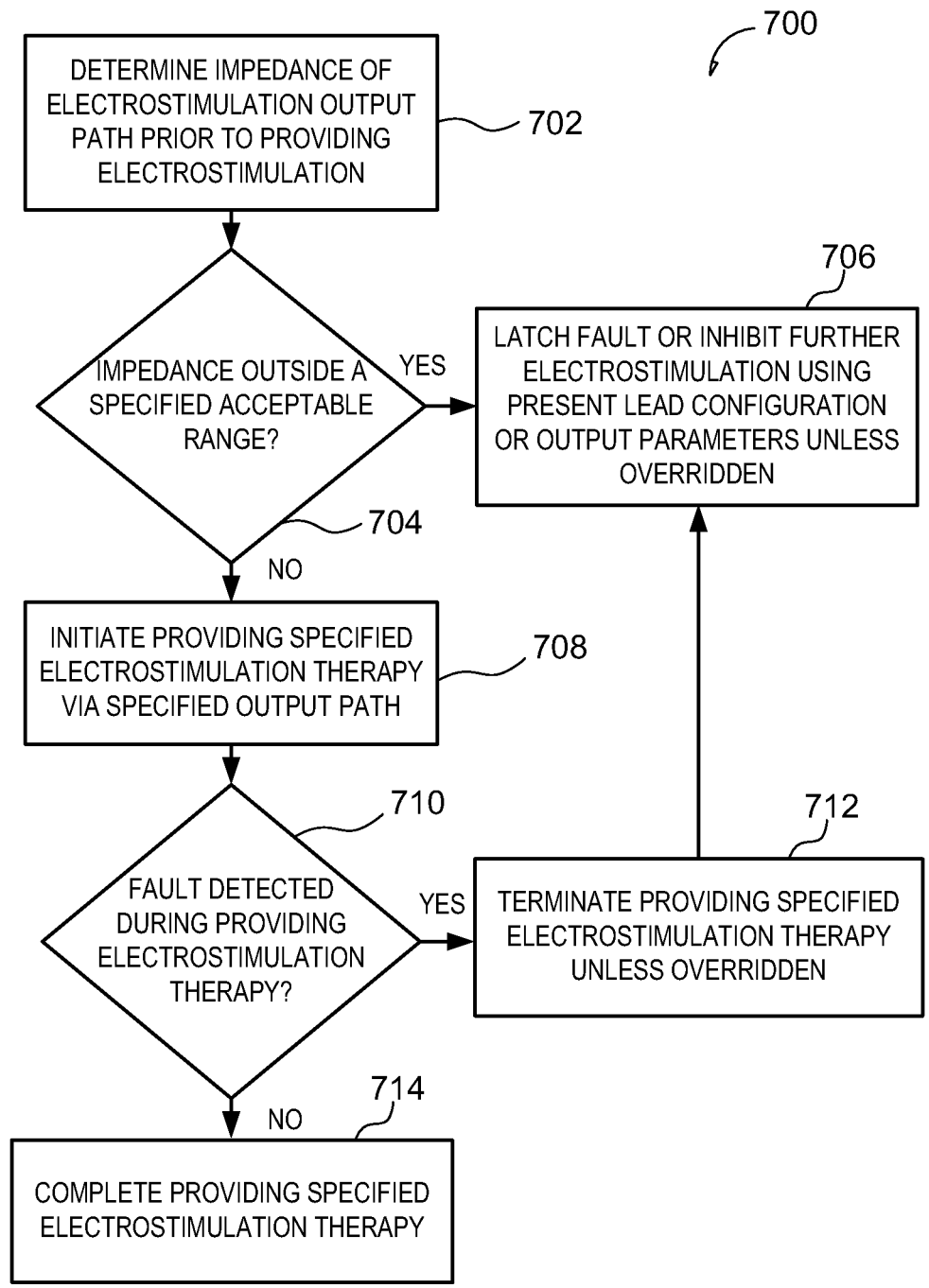
FIG. 7 illustrates generally an example that can include determining an impedance of an electrostimulation output path prior to providing an electrostimulation, and inhibiting electrostimulation if the impedance is outside a specified range.

FIG. 7 illustrates generally an example that can include determining an impedance of an electrostimulation output path prior to providing an electrostimulation, and inhibiting electrostimulation if the impedance is outside a specified range. At 702, an impedance of an electrostimulation output path can be determined, such as using a relatively low voltage or low energy (e.g., non-stimulating) impedance measurement, such as prior to delivery of cardioversion or defibrillation pulses. Such an impedance can include measuring a contribution from one or more leads, electrodes, or other interconnects in the path between the measurement circuit and tissue. Such an impedance measurement can also include a tissue contribution. For example, a synchronous current injection and voltage measurement can be used, such as discussed in relation to the physiologic impedance measurement techniques of U.S. patent application Ser. No. 12/350,728, entitled "IMPEDANCE MEASUREMENT AND DEMODULATION USING IMPLANTABLE DEVICE," filed on Jan. 8, 2009, assigned to Cardiac Pacemakers, Inc., which is herein incorporated by reference in its entirety, including its description of injecting one or more non-tissue-stimulating bi-phasic current pulses and synchronously measuring the voltage induced by the one or more bi-phasic current pulses.

At 704, the measured impedance can be compared to an acceptable range or to a specified threshold. In an illustrative example, the specified range can include an impedance from about 20 ohms to about 125 ohms. In another illustrative example, a specified threshold can be about 10 ohms. At 706, if the impedance is outside the specified range, or below a specified threshold, a fault can be latched, or further electrostimulation using the present electrostimulation lead configuration or output parameters can be inhibited, unless overridden.

At 708, if the impedance is within the specified acceptable range, or above a specified threshold, an electrostimulation therapy can be initiated. Such an electrostimulation can include providing one or more defibrillation or cardioversion pulses. In an example, as discussed above in the examples of FIGS. 1-6, the electrostimulation can be provided by a therapy circuit. For example, at 710, the therapy circuit can be monitored during the delivery of the electrostimulation. If 712, if a fault has been detected during delivery of the electrostimulation, the delivery can be terminated (e.g., truncated or otherwise cut off) unless overridden.

At 714, if no fault is detected during delivery of the electrostimulation, the entire specified electrostimulation energy can be delivered over the specified pulse duration (or, e.g., over a specified waveform duration if the specified electrostimulation includes multiple phases). In FIG. 7, a two-tiered approach can be used, such as including a low energy or low voltage impedance measurement to catch "hard" faults, and using one or more methods or circuits as shown in the examples of FIGS. 1-6 to catch dynamic faults, or faults that exhibit a non-linear response with respect to voltage (e.g., insulation failures, lead or conductor fractures, or the like).

One or more of the examples of FIGS. 1-7 can include logging or otherwise recording information about one or more faults. Such information can be later transmitted or otherwise communicated to one or more local or remote external assemblies, such as shown in FIG. 1, such as to alert a patient, physician, or other caregiver that a defect or fault has been encountered.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A system, comprising:
   a medical device, comprising:
   a processor circuit;
   a therapy circuit configured to provide a specified defibrillation therapy to a tissue site, the specified defibrillation therapy including a scheduled completion, the therapy circuit including a protection circuit configured to adjust specification of the specified defibrillation therapy being provided so as to provide an adjusted defibrillation therapy before the scheduled completion; and
   a monitoring circuit comprising a comparator, the monitoring circuit configured to monitor a therapy circuit defibrillation therapy output energy parameter using the comparator during providing the specified defibrillation therapy;
   wherein the comparator is configured to compare the therapy circuit defibrillation therapy output energy parameter with a specified threshold corresponding to a fault; and
   wherein the monitoring circuit is configured to trigger the protection circuit to adjust specification of the specified defibrillation therapy when the therapy circuit defibrillation therapy output energy parameter exceeds the specified threshold as indicated by the comparator;
   wherein the monitoring circuit and the protection circuit are configured to operate asynchronously with respect to the processor circuit and without requiring the intervention of the processor circuit.

2. The system of claim 1, wherein the protection circuit is configured to inhibit the therapy circuit from completing the specified defibrillation therapy.

3. The system of claim 1, wherein the monitoring circuit includes a latency of about 1 microsecond or less, the latency comprising an interval beginning when the therapy circuit defibrillation therapy output energy parameter exceeds the specified threshold and ending with an assertion of a trigger to the protection circuit by the monitoring circuit to inhibit the therapy circuit.

4. The system of claim 1, wherein the medical device includes a processor circuit; and
   wherein the monitoring circuit is coupled to the processor circuit and configured to provide a fault indication to the processor circuit when the therapy circuit defibrillation therapy output energy parameter exceeds the specified threshold as indicated by the comparator.

5. The system of claim 4, wherein the processor is configured to enable the therapy circuit to at least attempt to complete the specified defibrillation therapy, despite the fault indication, when an override is asserted.

6. The system of claim 5, wherein the processor includes a counter configured to count a number of faults; and
wherein the processor is configured to enable the therapy circuit to at least attempt to complete the specified defibrillation therapy when the count of the number of faults exceeds a specified count.

7. The system of claim 5, wherein the processor includes a timer configured to measure an arrhythmia episode duration; and
wherein the processor is configured to enable the therapy circuit to at least attempt to complete the defibrillation therapy when the arrhythmia episode duration exceeds a specified duration, despite the fault indication.

8. The system of claim 4, wherein the therapy circuit is configured to provide a defibrillation therapy using an adjusted defibrillation therapy output energy parameter provided by the processor in response to the fault indication, the adjusted defibrillation therapy output energy parameter including one or more of an adjusted current, an adjusted voltage, an adjusted power, or an adjusted energy, as compared to a specified defibrillation therapy output energy parameter that would be provided in the absence of the fault.

9. The system of claim 4, wherein the therapy circuit is configured to controllably provide the defibrillation therapy to one or more of a first electrode combination at or near the tissue site, or to a second electrode combination, using an electrode selection provided the processor circuit, and in response to the fault indication.

10. The system of claim 1, wherein the therapy circuit includes a conductor, wherein the defibrillation therapy output energy parameter includes an output current through the conductor, and wherein the comparator is configured to compare a voltage developed across a specified portion of the conductor with the specified threshold.

11. The system of claim 1, wherein the medical device includes an implantable medical device; and
wherein the system further comprises an implantable lead electrically and mechanically coupled to the implantable medical device, the implantable lead including an electrode implantable at or near the tissue site.

12. The system of claim 1, wherein the therapy circuit includes an insulated gate bipolar transistor (IGBT);
wherein the therapy circuit is configured to provide the defibrillation therapy at least in part using the IGBT; and
wherein the protection circuit is configured to control a gate of the IGBT to inhibit a conduction of the defibrillation therapy by the IGBT in response to a trigger provided by the monitoring circuit.

13. The system of claim 1, wherein the therapy circuit includes an insulated gate bipolar transistor (IGBT) coupled to a gate-turn-off (GTO) thyristor;
wherein the therapy circuit is configured to provide the defibrillation therapy at least in part using the GTO thyristor, and at least in part using the IGBT to control the conduction state of the GTO thyristor; and
wherein the protection circuit is configured to control a gate of the IGBT to inhibit conduction of the defibrillation therapy by the GTO thyristor in response to a trigger provided by the monitoring circuit.

14. An implantable medical device including a processor circuit and a memory circuit, the memory circuit including instructions that, when performed by the processor circuit, cause the implantable medical device to:
provide a specified defibrillation therapy to a tissue site using a therapy circuit, the specified defibrillation therapy including a scheduled completion;
monitor a therapy circuit defibrillation therapy output energy parameter using a monitoring circuit during the providing the specified defibrillation therapy, including comparing a therapy circuit defibrillation therapy output energy parameter to a specified threshold corresponding to a fault; and
adjust the specification of the specified defibrillation therapy being provided using a protection circuit when the therapy circuit defibrillation therapy output energy parameter exceeds the specified threshold so as to provide an adjusted defibrillation therapy before the scheduled completion;
wherein the monitoring circuit and the protection circuit are configured to operate asynchronously with respect to the processor circuit and without requiring the intervention of the processor circuit.

15. The implantable medical device of claim 14, wherein the instructions include instructions that cause the implantable medical device to:
provide a fault indication to the processor circuit in response to the therapy defibrillation therapy output energy parameter exceeding the specified threshold; and
enable the therapy circuit to at least attempt to complete the specified defibrillation therapy despite the fault indication.

16. The implantable medical device of claim 15, wherein the instructions include instructions that cause the implantable medical device to:
count a number of faults; and
enable the therapy circuit to at least attempt to complete the specified defibrillation therapy despite the fault indication when a count of the number of faults exceeds a specified count.

17. The implantable medical device of claim 15, wherein the instructions include instructions that cause the implantable medical device to:
measure an arrhythmia episode duration; and
enable the therapy circuit to at least attempt to complete the specified defibrillation therapy despite the information indicative of a fault when the arrhythmia episode duration exceeds a specified duration.

18. The implantable medical device of claim 15, wherein the instructions include instructions that cause the implantable medical device to:
provide an defibrillation therapy using an adjusted defibrillation therapy output energy parameter of the adjusted defibrillation therapy provided by the processor in response to the fault indication, the adjusted defibrillation therapy output energy parameter including one or more of an adjusted current, an adjusted voltage, an adjusted power, or an adjusted energy, as compared to a specified defibrillation therapy output energy parameter that would be provided in the absence of the fault.

19. The implantable medical device of claim 1, comprising a sensing element including a resistance provided by a trace on a printed wiring board;
wherein the therapy circuit defibrillation therapy output energy parameter includes an output current; and
wherein the monitoring circuit is configured to monitor the output current using the sensing element and the comparator.

* * * * *